(12) United States Patent
Lucas

(10) Patent No.: US 8,445,715 B2
(45) Date of Patent: May 21, 2013

(54) METHOD OF SYNTHESIZING FENOFIBRATE

(75) Inventor: Beatrice Lucas, Brognon (FR)

(73) Assignee: Synkem, Chenove (FR)

( * ) Notice: Subject to any disclaimer, the term of this patent is extended or adjusted under 35 U.S.C. 154(b) by 595 days.

(21) Appl. No.: 12/600,515

(22) PCT Filed: Jul. 2, 2008

(86) PCT No.: PCT/EP2008/058511
§ 371 (c)(1),
(2), (4) Date: Nov. 17, 2009

(87) PCT Pub. No.: WO2009/004029
PCT Pub. Date: Jan. 8, 2009

(65) Prior Publication Data
US 2012/0065421 A1   Mar. 15, 2012

(30) Foreign Application Priority Data

Jul. 2, 2007 (FR) .................... 07 56220

(51) Int. Cl.
*C07C 69/76* (2006.01)
*C07C 69/95* (2006.01)

(52) U.S. Cl.
USPC ........................................... 560/52

(58) Field of Classification Search
None
See application file for complete search history.

(56) References Cited

U.S. PATENT DOCUMENTS

| 4,072,705 A | 2/1978 | Mieville |
| 2004/0073058 A1 | 4/2004 | Guazzi |
| 2004/0132995 A1* | 7/2004 | Deshpande et al. .......... 540/222 |

FOREIGN PATENT DOCUMENTS

EP   0126361   11/1984

OTHER PUBLICATIONS

Treu et al. (J. Heterocyclic Chem., 2002, 39, 1283).*
http://www.chemicalland21.com/industrialchem/solalc/ISOPROPYL%20ACETATE.htm (Apr. 2012).*
http://en.wikipedia.org/wiki/Protic_solvent (Apr. 2012).*
Boros et al "Preparation of New 2,3-diphenylpropenoic Acid Esters-Good Yields Even for the More Hindered Z Isomers", Molecules, vol. 9, 2004, pp. 256-263.

* cited by examiner

*Primary Examiner* — Susanna Moore
*Assistant Examiner* — Jennifer C Sawyer
(74) *Attorney, Agent, or Firm* — Ladas & Parry LLP

(57) ABSTRACT

A novel process for the synthesis of fenofibrate, includes reacting a metal salt of fenofibric acid with an isopropyl halide, in a solvent system composed of a mixture of dimethyl sulfoxide and a $C_2$-$C_4$ alkyl acetate. The process can be used on an industrial scale and makes it possible to obtain a fenofibrate of a quality in accordance with the Pharmacopoeia without the need for purification by recrystallization.

15 Claims, No Drawings

METHOD OF SYNTHESIZING FENOFIBRATE

The invention relates to a novel process for the synthesis of fenofibrate.

PRIOR ART

Fenofibrate (methylethyl ester of 2-[4-(4-chlorobenzoyl)phenoxy]-2-methylpropanoic acid)

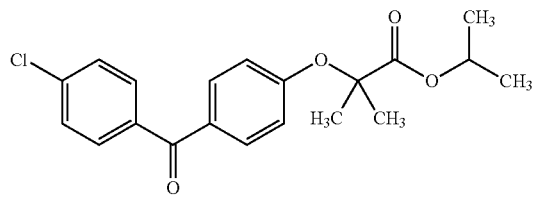 [SMILES: CC(C)OC(=O)C(C)(C)Oc1ccc(C(=O)c2ccc(Cl)cc2)cc1]

is an active substance known for treating hypertriglyceridemia and hypercholesterolemia.

This compound is an isopropyl ester of fenofibric acid and various processes have been provided for its industrial manufacture.

Thus, fenofibrate is preferably obtained with a good yield by reaction of 4-chloro-4'-hydroxybenzophenone with isopropyl 2-bromo-2-methylpropanoate in the absence of solvent and in the presence of an alkaline agent, such as, in particular, potassium carbonate (EP 0 245 156 B1).

The document WO 02/062743 discloses a process for the preparation of fibrates similar to the preceding process but in which the phenol is reacted with an alkyl 2-bromo-2-methylpropionate in the presence of potassium bicarbonate and in a solvent chosen from $C_1$-$C_4$ ketones and alcohols. The only example described in this document relates to fenofibrate and the solvent used is isopropanol. However, the reaction time is much greater than in the case of the solvent-free process.

The document EP 0 002 151 discloses a different process according to which the methyl ester of 2-methyl-2-phenoxypropanoic acid is reacted with 4-chlorobenzoyl chloride or 4-chlorobenzoic anhydride in a halogenated solvent in the presence of a Lewis acid, such as boron trifluoride (Friedel-Crafts reaction). However, this process does not give satisfactory results if the isopropyl ester is used, which would make it possible to obtain fenofibrate directly, and the manufacture of fenofibrate then requires a transesterification in the presence of sodium isopropoxide.

The processes described in patent applications FR 2 035 821, FR 2 157 853 (certificate of addition to French patent FR 2 035 821), FR 2 300 552 and FR 2 342 723 are also known. Among the latter processes, one method of industrial synthesis consists in:

a) preparing 4-chloro-4'-hydroxybenzophenone by a Friedel-Crafts reaction between 4-chlorobenzoyl chloride and anisole, followed by demethylation of the compound obtained, b) preparing 2-[4-(4-chlorobenzoyl)phenoxy]-2-methylpropanoic acid by reaction of the acetone/chloroform mixture in an alkaline medium ("Bargellini" reaction) with 4-chloro-4'-hydroxybenzophenone, c) preparing fenofibrate by esterification of the acid with isopropyl alcohol in an acidic medium, for example in the presence of sulfuric acid.

The latter method exhibits the advantage of using inexpensive reactants and thus of producing fenofibrate with an advantageous material cost. However, the industrial implementation of the esterification stage requires large amounts of sulfuric acid in order to obtain good reaction kinetics, which results in frequent processing difficulties.

Furthermore, synthetic methods for obtaining an ester starting from a carboxylic acid which involve the reaction of an alkyl halide with a metal salt of said carboxylic acid are known from the literature. For example, the publication Molecules, 2004, 9, 256-263, provides the reaction of E- or Z-2,3-diphenylpropenoic acid with isopropyl bromide in order to obtain the corresponding isopropyl ester. However, the yields are low, in the region of 36 to 38%, which is not compatible with industrial production.

U.S. Pat. No. 3,649,655 describes the preparation of cyclohexyl acetate by reaction of cyclohexyl bromide with acetic acid in the presence of an inorganic catalyst, such as ferric chloride. In this case again, the reaction yields do not exceed 66%.

More recently, the publication Tetrahedron Letters, 46 (2005), 3641-3644, discloses good yields (in the region of 85 to 94%) for the preparation of isopropyl esters starting from 2-bromopropane and variously substituted benzoic acids. However, the reaction is carried out in an ionic liquid solvent [trihexyl(tetradecyl)phosphonium bis(trifluoromethylsulfonyl)amide], the use of which on the industrial scale does not appear to be possible to envisage for the time being.

OBJECT OF THE INVENTION

It has now been discovered, which constitutes the basis of the invention, that it is possible to carry out the esterification of fenofibric acid with an isopropyl halide in order to obtain fenofibrate under economical conditions entirely compatible with manufacture on industrial scale, that is to say the production of several hundred tonnes per annum, by choosing a specific solvent for the reaction.

More specifically, it has been discovered, entirely unexpectedly, that the use of a solvent composed of a mixture in any proportions of dimethyl sulfoxide (DMSO) and of a $C_2$-$C_4$ alkyl acetate enables direct access to fenofibrate in agreement with the quality standards of Pharmacopoeia, without requiring additional purification by recrystallization.

The process for the preparation of fenofibrate according to the invention is thus characterized in that it consists in reacting, in a solvent composed of a mixture of dimethyl sulfoxide and of a $C_2$-$C_4$ alkyl acetate, a metal salt of fenofibric acid with an isopropyl halide.

In other words, the present invention relates to a novel process for producing fenofibrate starting from fenofibric acid, in which the esterification reaction is carried out using an alkyl halide and is performed in a specifically chosen solvent, according to the following reaction scheme:

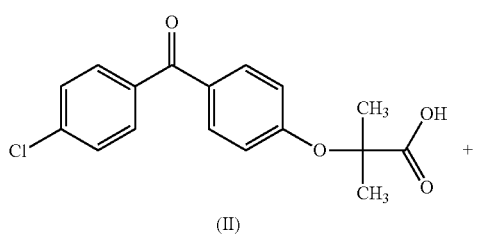

(II)

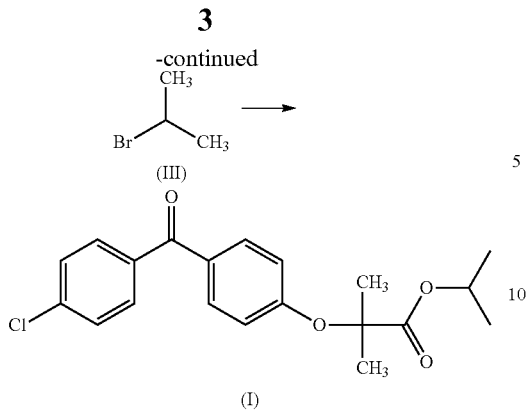

A general embodiment of the invention consists in reacting fenofibric acid with an inorganic base in a solvent system composed of a mixture of dimethyl sulfoxide and of a $C_2$-$C_4$ alkyl acetate, so as to obtain a metal salt of fenofibric acid, such as, for example, a potassium or sodium salt, and then this salt is reacted with an isopropyl halide, at a temperature close to the reflux temperature of the reaction mixture at atmospheric pressure, in order to obtain fenofibrate in solution in the mixture.

The novelty of the present invention lies in the choice of the solvent system used for carrying out the reaction represented by the preceding reaction scheme.

It has been discovered that the combination of dimethyl sulfoxide and of a $C_2$-$C_4$ alkyl acetate makes it possible to carry out the abovementioned reaction under the best conditions and to directly obtain a product in agreement with the quality standards of Pharmacopoeia comprising no impurity at a level greater than 0.05%.

In this context, it has been shown:
  on the one hand, that dimethyl sulfoxide (DMSO) allows both a good chemical yield and a good quality of the fenofibrate obtained, and
  on the other hand, that the joint use of DMSO and of a $C_2$-$C_4$ alkyl acetate, preferably isopropyl acetate, makes it possible to carry out the reaction under the best conditions and to directly obtain a product in agreement with the quality standards of Pharmacopoeia.

The amounts of dimethyl sulfoxide and of $C_2$-$C_4$ alkyl acetate used in the context of the present invention can vary within wide limits.

Excellent results have been obtained by carrying out the reaction with an amount of dimethyl sulfoxide so that the DMSO/fenofibric acid ratio (expressed by weight) is comprised between 0.1 and 2 and preferably comprised between 0.2 and 1.

According to a currently preferred embodiment, use will be made of a mixture of DMSO and of alkyl acetate so that the ratio of the total weight of solvent to the weight of the fenofibric acid is comprised between 0.2 and 3 and more preferably comprised between 0.4 and 2.

The isopropyl halide is preferably isopropyl bromide (also known as 2-bromopropane).

The metal salt of fenofibric acid is generally prepared by reaction (preferably carried out in the reaction medium) between fenofibric acid and a base, preferably an inorganic base.

Mention may be made, among the inorganic bases capable of being used to prepare the metal salt of fenofibric acid, of potassium hydroxide, potassium carbonate, potassium bicarbonate, sodium hydroxide, sodium carbonate or sodium bicarbonate, and also lithium hydroxide, lithium carbonate, calcium hydroxide or calcium carbonate.

Excellent results have been obtained using potassium carbonate, which thus constitutes a particularly preferred inorganic base.

According to a preferred embodiment of the invention, fenofibric acid is salified with potassium carbonate and the potassium salt obtained is reacted with isopropyl bromide in the same reaction medium.

DETAILED DESCRIPTION OF THE INVENTION

According to a general procedure of the process according to the invention, a mixture composed of fenofibric acid and of the solvent system is first prepared, followed by addition of a stoichiometric amount of a basic inorganic component capable of forming a salt with fenofibric acid. Use is more particularly made of potassium carbonate in order to obtain the potassium salt of fenofibric acid. An amount of an isopropyl halide (preferably 2-bromopropane) slightly greater than stoichiometric is subsequently added to the reaction mixture and the resulting mixture is brought to gentle reflux for 2 to 8 hours. The insoluble inorganic salts are removed by filtration and the solvent of the reaction is also removed and replaced by the crystallization solvent of fenofibrate. After cooling, the crystallized fenofibrate is isolated by filtration on a filtering device and dried.

The following example, which describes a procedure carried out on a laboratory scale, allows for a better understanding of the invention. This example should not, however, be regarded as limiting and the salification reactant, the isopropyl halide and the solvents can be modified without departing from the scope of the invention.

EXAMPLE I

2-[4-(4-Chlorobenzoyl)phenoxy]-2-methylpropanoic acid, 1-methylethyl ester 1 kg (3.14 mol) of fenofibric acid (II), 500 ml of dimethyl sulfoxide and 1 l of isopropyl acetate were charged into a jacketed 5 l reactor under nitrogen. 433.5 g (3.14 mol) of potassium carbonate were then added, with stirring at ambient temperature, and the reaction mixture was brought to 85-90° C. for 45 min. The temperature of the reaction mixture was subsequently reduced to approximately 80° C. and 354 ml (3.77 mol) of 2-bromopropane and then 100 ml of isopropyl acetate were added over a period of 50 min. The mixture was kept stirring at 85-95° C. for 5 hours and then slightly cooled to approximately 80° C. In-process monitoring showed that the degree of conversion to give fenofibrate was approximately 99.5%. The content of the reactor was hot-filtered and the salts separated on the filter were washed with 1 l of isopropyl acetate, which was combined with the filtrate. The isolated salts, which essentially comprise potassium bromide, were dried and kept for recycling. The filtrate was concentrated under reduced pressure while maintaining a bulk temperature of approximately 80° C., and of 95° C. at the end of concentrating. After removal of the solvents, 2.27 l of isopropanol and 455 ml of pure water were added. The mixture was brought to gentle reflux for 10 min and then hot-filtered. Under stirring, the filtrate was slowly cooled down to a temperature of 0° C. The crystallized fenofibrate was separated by filtration on a filtering device, washed on the filtering device with approximately 500 ml of ice-cold isopropanol and then dried under vacuum at 45-50° C. 1075 g of fenofibrate with a purity of greater than 99.5% and comprising no impurity at a level of greater than 0.05% were thus obtained (yield=94.9%).

This process can be adapted to an industrial reactor (stainless or enameled steel) which makes possible the production of batches of approximately 1000 kg with 4000 l reactors under reaction time and capacity conditions compatible with an excellent productive output.

The process according to the invention allows direct access to a product in agreement with the quality standards of Pharmacopoeia without the need for purification by recrystallization. These various aspects are also highly advantageous from the viewpoint of the protection of the environment since the by-products of the reaction are limited in amount and for the most part can be recycled. With respect to this specific point, it is also noteworthy that the entire process uses a very small amount of water and does not produce any wastes in the form of saline aqueous solutions.

What is claimed is:

1. A method for the preparation of fenofibrate, comprising reacting a metal salt of fenofibric acid with an isopropyl halide in a solvent comprising a mixture of dimethyl sulfoxide and a $C_2$-$C_4$ alkyl acetate.

2. The method as claimed in claim 1, wherein said solvent is a mixture of dimethyl sulfoxide and isopropyl acetate.

3. The method as claimed in claim 1 or 2, wherein the dimethyl sulfoxide and fenofibric acid are present in dimethyl sulfoxide: fenofibric acid weight ratio of between 0.1 and 2.

4. The method as claimed in claim 1 or 2, wherein said solvent is used in an amount such that a ratio of total weight of solvent to weight of fenofibric acid is between 0.2 and 3.

5. The method as claimed in claim 4, wherein the ratio of the total weight of solvent to the weight of fenofibric acid is between 0.4 and 2.

6. The method as claimed in claim 1 or 2, wherein the isopropyl halide is isopropyl bromide (or 2-bromopropane).

7. The method as claimed in claim 1 or 2, wherein the metal salt of fenofibric acid is selected from the group consisting of a potassium salt, a sodium salt, a lithium salt and a calcium salt.

8. The method as claimed in claim 7, wherein the metal salt of fenofibric acid is a potassium salt.

9. The method as claimed in claim 3, wherein the dimethyl sulfoxide: fenofibric acid weight ratio is between 0.2 and 1.

10. The method as claimed in claim 3, wherein said solvent is used in an amount such that a ratio of total weight of solvent to weight of fenofibric acid is between 0.2 and 3.

11. The method as claimed in claim 3, wherein the isopropyl halide is isopropyl bromide (or 2-bromopropane).

12. The method as claimed in claim 4, wherein the isopropyl halide is isopropyl bromide (or 2-bromopropane).

13. The method as claimed in claim 3, wherein the metal salt of fenofibric acid is a potassium salt.

14. The method as claimed in claim 4, wherein the metal salt of fenofibric acid is a potassium salt.

15. The method as claimed in claim 6, wherein the metal salt of fenofibric acid is a potassium salt.

* * * * *